United States Patent [19]

Charters et al.

[11] Patent Number: 4,938,223
[45] Date of Patent: Jul. 3, 1990

[54] TRANSCUTANEOUS NERVE BLOCK DEVICE

[75] Inventors: Thomas H. Charters, Beaverton, Oreg.; Fritz L. Jenkner, Vienna, Austria

[73] Assignee: T. H. Charters, Inc., Beaverton, Oreg.

[21] Appl. No.: 174,233

[22] Filed: Mar. 28, 1988

[51] Int. Cl.$^5$ ............................................. A61N 1/36
[52] U.S. Cl. ...................................................... 128/421
[58] Field of Search ................................. 128/421–423, 128/420, 420.5

[56] References Cited

U.S. PATENT DOCUMENTS

| | | | |
|---|---|---|---|
| 3,294,092 | 12/1966 | Landauer | 128/420 R |
| 3,766,331 | 10/1973 | Zink | 128/420.5 |
| 4,210,151 | 7/1980 | Keller, Jr. | 128/421 |
| 4,230,121 | 10/1980 | Stanton | 128/422 |
| 4,573,449 | 3/1986 | Warnke | 128/422 X |
| 4,580,570 | 4/1986 | Sarrell et al. | 128/423 R X |
| 4,690,145 | 9/1987 | King-Smith et al. | 128/421 |
| 4,754,759 | 7/1988 | Allocca | 128/421 |
| 4,784,142 | 11/1988 | Liss et al. | 128/421 |

OTHER PUBLICATIONS

Relorette Schematic (representative sketch by applicants).
Jenkner, F. L., "TEN Block", Manual for Amer. Assn. of Orthopedic Medicine, (1986).
Jenkner, F. L. et al., "Transdermal Transcutaneous Electric Nerve Stimulation for Pain", Applied Neurophys. vol. 44, No. 5-6, (pp. 330–337), 1981.

Primary Examiner—Francis Jaworski
Attorney, Agent, or Firm—Dellett, Smith-Hill & Bedell

[57] ABSTRACT

A transcutaneous electrical nerve block device generates an improved stimulation signal waveform to provide improved pain relief. Bursts of stimuli include stimuli having waxing and waning amplitudes which bear a consistent relationship to the magnitude of the stimuli burst, the bursts of stimuli being more tolerable at higher intensities. The bursts of stimuli are further modulated in amplitude to aid in prevention of adaptation by the patient to the stimulation.

19 Claims, 4 Drawing Sheets 4,938,223

TRANSCUTANEOUS NERVE BLOCK DEVICE

BACKGROUND OF THE INVENTION

The present invention relates generally to pain relief devices and particularly to devices for nerve blocking through transcutaneous application of electric current.

The procedure commonly known as transcutaneous electric nerve stimulation for pain reduction involves the application of electric current to the skin by way of plural electrodes. For certain forms of application it has been found that the effect is more aptly described as a blocking rather than a stimulating action. Such blocking action can provide prolonged pain relief but its effectiveness depends on various characteristics of the stimulating current and electrode placement. In particular it has been shown that waveform characteristics of the stimulating signal can determine results achieved in the reduction of pain. Accordingly, research directed to the optimum stimuli waveform is significant in the area of electrical nerve blocking.

Heretofore, stimulus waveforms have been characterized by bursts of pulses having substantially waxing and waning amplitudes achieved through modulating the amplitude of a pulse signal to provide a burst for each cycle of a modulating envelope. Because the pulse signal and the modulating signal have had no predetermined timed relationship, the waxing and waning characteristics are unpredictable. That is to say, the amplitude of pulses within each burst do not bear a consistent relationship to the amplitude of the burst in which they occur, whereby the amplitude of the first pulse of a given burst can vary widely. As a result, the stimulation can become irritating rather than corrective unless overall signal intensity is limited. The patient can then accommodate or adapt to the corrective signal.

SUMMARY OF THE INVENTION

A transcutaneous nerve block device according to the present invention produces a stimulation signal which provides improved pain reduction. According to one aspect of the present invention a stimulating waveform includes bursts of stimuli having waxing and waning amplitudes wherein each stimulus in each burst bears a consistent relationship with the amplitude of the burst in which it occurs, e.g., the amplitude of the first stimulus of each burst is a fixed percentage of the amplitude of the burst in which it occurs, the amplitude of the second stimulus of each burst is a fixed percentage of the amplitude of the burst in which it occurs, etc. According to another aspect of the present invention, amplitude variation or swelling of modulated stimuli is provided. As a consequence, stimuli of substantial amplitude can be employed without producing counter productive discomfort, and without the patient accommodating or "adapting" to the stimulus waveform so as to reduce its effectiveness.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DRAWINGS

DETAILED DESCRIPTION

Figure 1:
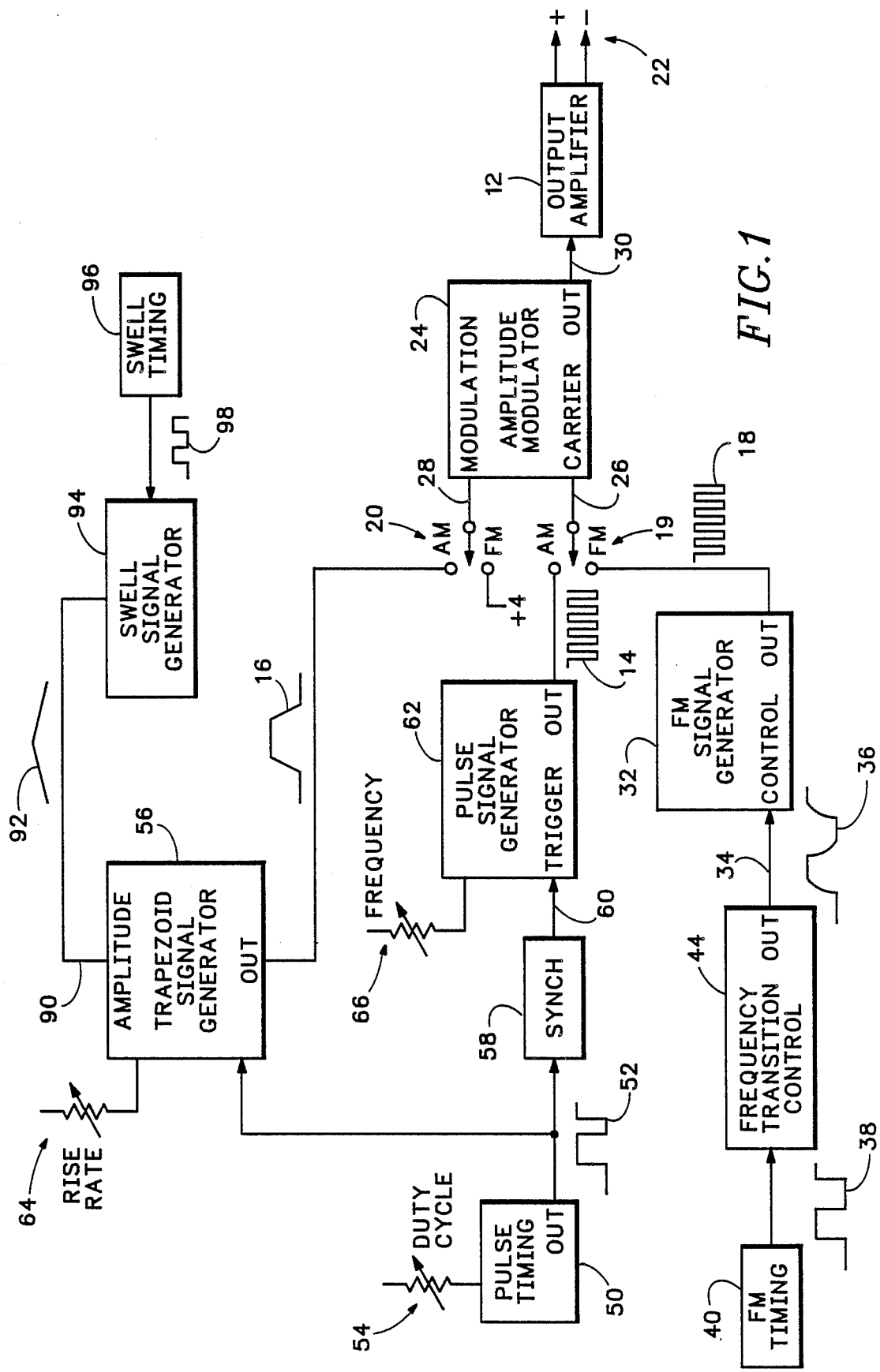
FIG. 1 is a block circuit diagram of a preferred embodiment of the present invention.

Referring to FIG. 1, an output amplifier block 12 selectively amplifies either a pulse signal 14 as modulated in amplitude by a trapezoid signal 16, or an FM signal 18, the selection being a function of the position of switches 19 and 20 each having an FM contact and an AM contact. The output of amplifier block 12 is provided to electrodes 22 for cutaneous coupling to a patient receiving pain relief treatment.

An amplitude modulator block 24 includes a carrier terminal 26 connected to the movable contact of switch 19, a modulation terminal 28 coupled to the movable contact of switch 20, and an output terminal 30 for driving amplifier block 12. The signal provided at carrier terminal 26 is modulated in amplitude in accordance with the magnitude of a signal provided at modulation terminal 28 and is thence supplied at output terminal 30. The AM contact of switch 19 receives pulse signal 14 while the FM contact of switch 19 receives FM signal 18. The FM contact of switch 20 is held to a constant 4 volts and the AM contact of switch 20 receives trapezoid signal 16.

Thus, when switches 19 and 20 are both set to the FM position, FM signal 18 is input via switch 19 to amplitude modulation block 24 at carrier signal terminal 26 while modulation terminal 28 receives a constant 4 volts. FM signal 18 is then passed through block 24 to amplifier 12 without amplitude modulation, i.e., with a substantially constant amplitude. When switches 19 and 20 are set to their AM contacts, pulse signal 14 is provided at carrier signal terminal 26 and trapezoid signal 16 is presented at modulation terminal 28. Pulse signal 14 is amplitude modulated in accordance with the magnitude of trapezoid signal 16 and appears in the form of bursts of stimuli at output terminal 30.

FM signal generator block 32 provides FM signal 18 to the FM contact of switch 19 and has a control input terminal 34 for adjusting the frequency of FM signal 18 in accordance with the magnitude of a frequency control signal 36. Frequency control signal 36 is varied between two levels to provide frequency alternation, e.g. between 3 Hz and 30 Hz. Transitions between frequency control voltages are determined by state changes in square wave FM timing signal 38 generated by an FM timing block 40.

Figure 2:
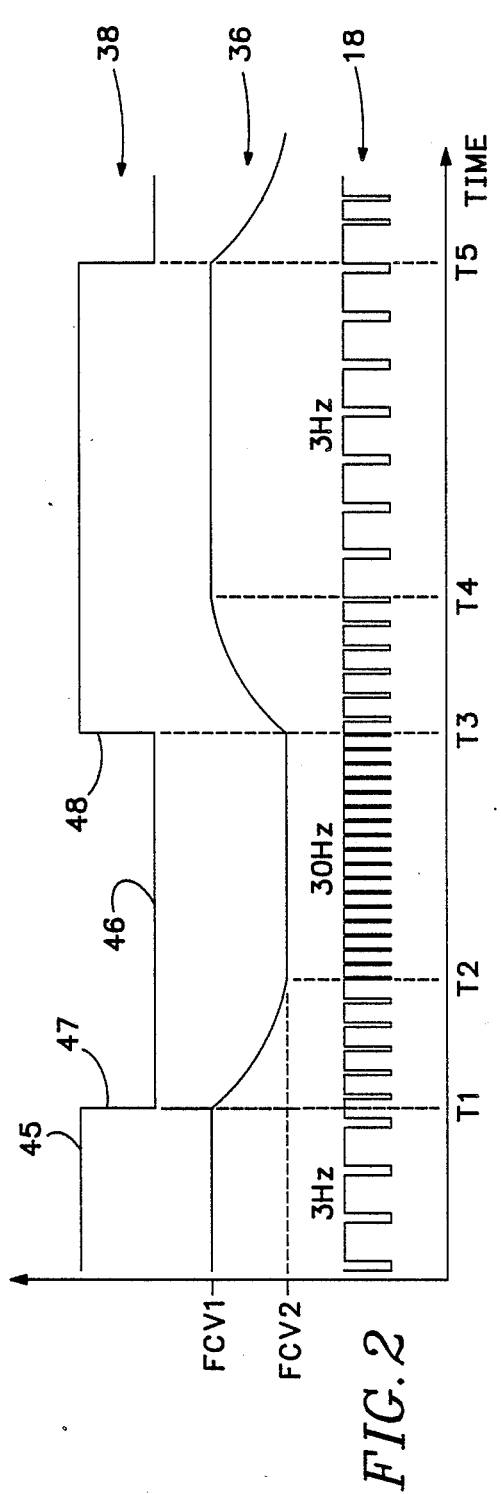
FIG. 2 is a timing diagram illustrating a frequency modulated stimulation signal.

Referring to FIG. 2 and viewing the same in conjunction with FIG. 1, as FM timing signal 38 varies between a first state 45 and a second state 46, frequency transition control block 44 varies the voltage of control signal 36 between frequency control voltages FCV1 and FCV2, respectively, avoiding a sudden change therebetween to provide a suitable transition in frequency for FM signal 18. When the voltage of frequency control signal 36 is at FCV1, FM signal 18 is constant at 3 HZ, and then increases to 30 Hz when frequency control signal 36 reaches FCV2. A frequency modulation cycle begins with a transition 47 in FM timing signal 38. FM signal 18 increases in frequency from 3 Hz to 30 Hz during a time T2—T1 of approximately 1 second. It remains at 30 Hz for a time T3—T2, approximately the next 2 seconds, until the next transition 48 in timing signal 38 at which time the frequency of FM signal 18 is lowered in a continuous manner back to 3 Hz, i.e., during a 1 second interval T4—T3. The signal remains at 3 Hz until a time T5, approximately 2 seconds later, after which the cycle repeats.

Referring again to FIG. 1, pulse timing block 50 supplies a 5 Hz square wave pulse timing signal and is provided with an adjustment 54 for changing the duty cycle of the pulse timing signal. The initial duty cycle is suitably set at 70%. Signal 52 is utilized by trapezoid signal generator block 56 for controlling production of trapezoid signal 16, and is also employed by a synchronization block 58 which activates a trigger input 60 of pulse signal generator block 62 to initiate a sequence of cycles in pulse signal stream 14. Pulse signal generator block 62 is provided with an adjustment 66 for changing the frequency of pulse signal 14. The latter is suitably initially set to a 99% duty cycle and has a frequency of 100 Hz.

Trapezoid signal generator block 56 has an adjustment 64 for changing the rise rate of trapezoid signal 16. As will be more fully explained hereinafter, a falling edge in timing signal 52 initiates a cycle, or a rising ramp, in trapezoidal signal 16, and the rising edge of timing signal 52 causes a falling ramp in trapezoidal signal 16. The trapezoid signal 16 waveform has a substantially linear rise, a constant magnitude center portion, and a linear fall.

Pulse timing signal 52 is employed to establish a predetermined relationship between trapezoid signal 16 and pulse signal 14 whereby a sequence of pulse signal 14 cycles is initiated in synchronism with and substantially at the beginning of a cycle of trapezoid signal 16. Synchronization block 58 detects a falling edge in timing signal 52 and activates trigger input 60 to initiate a first cycle in a sequence of cycles of pulse signal 14 substantially concurrently with a cycle in trapezoid signal 16.

Figure 3:
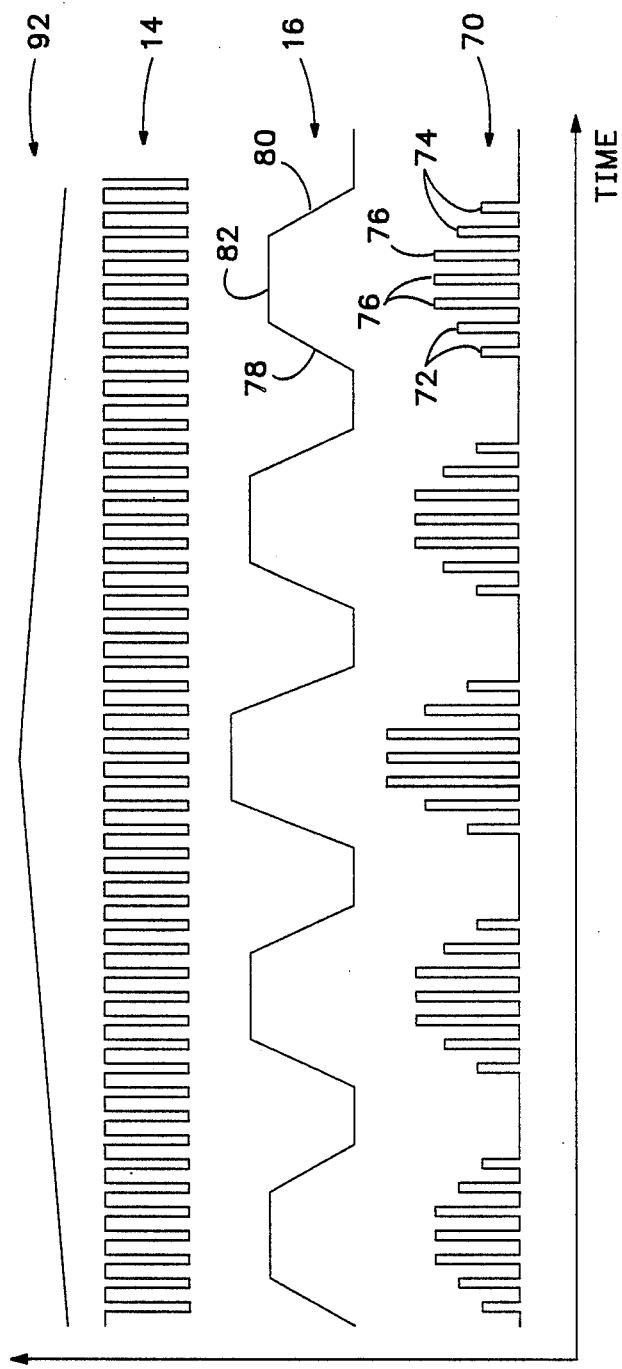
FIG. 3 is a timing diagram illustrating an amplitude modulated stimulation signal.

Referring now to FIG. 3 and viewing the same in conjunction with FIG. 1, when pulse signal 14 is amplitude modulated in accordance with trapezoid signal 16, a stimuli burst 70, having stimuli corresponding in frequency to pulse signal 14 and in amplitude to the magnitude of trapezoid signal 16, appears at output terminal 30 of amplitude modulation block 24. Stimuli within each burst 70 have waxing amplitudes 72 and waning amplitudes 74 separated by constant amplitude pulses 76. These amplitudes correspond, respectively, to linearly increasing region 78, linearly decreasing region 80, and central constant region 82 of each cycle in trapezoid signal 16.

Adjustment 66, affecting the frequency of pulse signal 14, determines the number of stimuli in each burst 70. In the presently described embodiment, the frequency of pulse signal 14 is such that a sequence of 9 cycles in pulse signal 14 occurs for each cycle in trapezoid signal 16; however, because pulse signal 14 is amplitude modulated by trapezoid signal 16 only the middle 7 cycles of the aforementioned sequence of 9 cycles of pulse signal 14 occur while trapezoid signal 16 has a substantially non-zero magnitude. Accordingly, each burst 70 includes 7 individual stimuli having substantially non-zero magnitude. Adjustment 64, affecting the rise rate of trapezoid signal 16, is desirably adjusted such that constant region 82 begins between the third and fourth cycles in the sequence of nine cycles in pulse signal 14. As a result, the first two stimuli in each burst 70 comprise the stimuli having waxing amplitudes 72 and the third stimuli in each burst 70 is the first of the stimuli having constant amplitudes 76. Adjustment 54, affecting the duty cycle of timing signal 52 and thereby determining the length of constant region 82 of trapezoid signal 16, is desirably adjusted to cause linearly decreasing region 80 to begin between the sixth and seventh cycles in the sequence of nine cycles in pulse signal 14. In this manner, the stimuli having constant amplitude 76 comprise the third, fourth, and fifth stimuli and the stimuli having waning amplitudes 74 comprise the sixth and seventh stimuli of each burst 70.

By establishing a predetermined timing relationship, or synchronization, between a sequence of cycles in pulse signal 14 and a cycle in trapezoid signal 16 and by adjusting the duration of regions 78, 80, and 82 with respect to cycles in pulse signal 14, each of the stimuli in bursts 70 bear a consistent relationship to the amplitude of burst 70 in which they occur. More particularly, the amplitude of the first and seventh stimuli in each burst 70 is approximately 40% of the amplitude of burst 70. The second and sixth stimuli amplitude is approximately 80% of the amplitude of burst 70, while the amplitude of the third, fourth and fifth stimuli in each burst 70 are 100% of the amplitude of the burst in which they occur. It has been found that such a stimulation signal provides improved pain relief. At the same time the signal is less irritating to the patient because of the gradual increase in intensity of the first three pulses and the gradual decrease in intensity of the last three pulses within each burst 70.

It is further believed that additional amplitude modulation of stimuli bursts 70 also improves pain relief by reducing the body's adaptation to the stimuli thereby increasing the physiological effectiveness of the stimuli. To this end, an amplitude determining terminal 90 of trapezoid generator block 56 receives a triangular swell signal 92 from swell signal generator block 94. Variations in the magnitude of swell signal 92 produce amplitude variations in trapezoid signal 16 which further result in amplitude variations among bursts 70. A swell timing block 96 provides a 1 Hz square wave swell timing signal 98 to swell signal generator block 94, the state of swell timing signal 98 determining the magnitude or rise and fall of swell signal 92. As can be seen in FIG. 3, stimuli bursts 70 vary in amplitude, by approximately 12%, in accordance with amplitude variations in swell signal 92.

Figure 4:
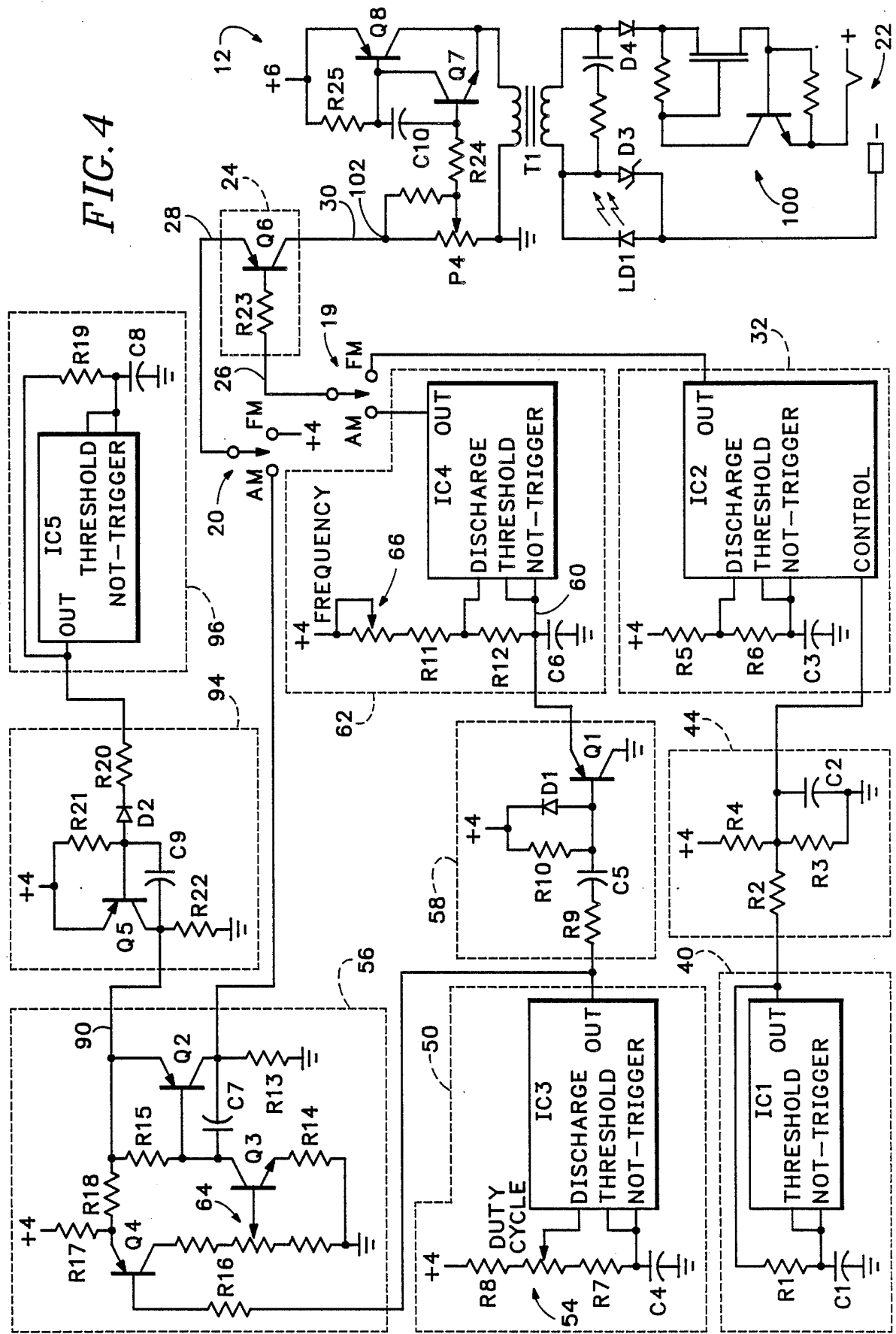
FIG. 4 is a more detailed diagram of the circuit of FIG. 1.

FIG. 4 illustrates, in greater detail, the preferred embodiment of the present invention shown in FIG. 1, wherein commercially available IC timers are used to implement portions of the invention. In particular, FIG. 4 illustrates the use of general purpose CMOS timers, Intersil model ICM7555 or ICM7556, which require a low supply current and are well suited for portable battery operated transcutaneous nerve block devices. The aforementioned devices will hereafter be referred to as IC timers for convenience and the various pins thereof will be referenced by their functional name, such as THRESHOLD, NOT-TRIGGER, OUT, DISCHARGE, AND CONTROL. As will be appreciated, complete documentation of these IC timers is readily available from the manufacturer.

FM timing block 40 includes an IC timer IC1 having its THRESHOLD and NOT-TRIGGER pins tied together and returned to ground through an external capacitor C1. The OUT pin is coupled to the THRESHOLD and NOT-TRIGGER pins through a resistor R1 and supplies FM timing signal 38. In this configuration IC1 is connected to trigger itself and free runs as a multivibrator such that FM timing signal 38 has a 50% duty cycle and a 1/6 Hz frequency. The frequency is dependent on the resistance and capacitance of R1 and C1, respectively, and is calculated as follows:

$$f = 1/(1.4\ RC)$$

where f is the resulting frequency of FM timing signal 38, R is the resistance of R1, and C is the capacitance of C1.

Frequency transition control block 44 receives FM timing signal 38 from the OUT pin of IC1 via resistor R2 and provides frequency control signal 36. The second terminal of resistor R2 is returned to ground through capacitor C2 and resistor R3 in parallel. The second end of resistor R2 is also connected to +4 volts through a resistor R4. Frequency control signal 36, at the junction of resistors R3 and R4, essentially follows timing signal 38, while sudden voltage changes are avoided by virtue of capacitor C2. The magnitudes of the voltage levels FCV1 and FCV2 in frequency control signal 36 are determined by the magnitude of FM timing signal 38 and by resistors R2, R3 and R4.

FM signal generator block 32 includes an IC timer IC2 receiving frequency control signal 36 at its CONTROL pin and having its THRESHOLD and NOT-TRIGGER pins connected together and grounded through an external capacitor C3. Serially connected resistors R5 and R6 couple the THRESHOLD and NOT-TRIGGER pins to +4 volts while the DISCHARGE pin of IC2 is tied to the interconnection of resistors R5 and R6. The OUT pin of IC2 is connected to the FM contact of switch 19 to provide FM signal 18. Thus, generating block 32 produces a regular series of pulses having a repetition rate governed by control signal 36. FM signal 18 is available at the FM contact of switch 19 and continuously iterates in frequency between 3 Hz and 30 Hz.

Generation of pulse signal 14 begins in pulse timing block 50 which includes IC timer IC3 having its THRESHOLD and NOT-TRIGGER pins returned to ground through an external capacitor C4 and coupled to adjustment potentiometer 54 through a resistor R7. The remaining terminal of potentiometer 54 is coupled to +4 volts through a resistor R8, while the movable contact of potentiometer 54 is connected to the DISCHARGE pin of IC3. Pulse timing signal 52 appears at the OUT pin of IC3 with its duty cycle being determined according to adjustment of the potentiometer 54.

Synchronization block 58 includes a resistor R9 and a capacitor C5 in series coupling the pulse timing signal 52 from the OUT pin of IC3 to the base of PNP transistor Q1 having its collector returned to ground and its emitter connected to trigger input 60 of pulse signal generator block 62. The base of transistor Q1 is coupled to +4 volts by way of resistor R10 and diode D1 in parallel. When a falling edge in pulse timing signal 52 is presented to synchronization block 58, a charging current flows through resistor R10 and into capacitor C5 which lowers the potential at the base of transistor Q1 and turns transistor Q1 on, thereby lowering trigger input 60 of pulse generator block 62 to ground level for discharging capacitor C6. A short time later, when capacitor C5 is charged and the charging current through resistor R10 ceases, transistor Q1 turns off causing pulse generator block 62 to generate a sequence of cycles in pulse signal 14 thus having timed relationship with pulse timing signal 52.

Pulse signal generator block 62 includes IC timer IC4 which has its THRESHOLD and NOT-TRIGGER pins connected together to form trigger input 60. The THRESHOLD and NOT-TRIGGER pins of IC4 are returned to ground via external capacitor C6 and coupled to potentiometer 66 by way of serially connected resistors R11 and R12, while the DISCHARGE pin of IC4 is tied to the interconnection of resistors R11 and R12. Potentiometer 66 is interposed between +4 volts and resistor R11 and has a movable contact also coupled to +4 volts. Pulse signal 14, taken from the OUT pin of IC4 and provided at the AM contact of switch 19, begins a cycle after trigger input 60 of pulse signal generator block 62 momentarily drops to ground potential, i.e., when transistor Q1 is momentarily turned on in response to a falling edge of pulse timing signal 52. Thus, IC4 provides a repetitive pulse signal 14 at the AM contact of switch 19 as synchronized by input 60. Sequences of pulses in AM signal 14 are then synchronized with respect to cycles in trapezoid signal 16 such that each triggered sequence of signal 14 pulses is "stationary" with respect to each cycle in signal 16. In this manner, when AM signal 14 is modulated in amplitude by trapezoid signal 16, the amplitude of stimuli within each burst 70 bear a consistent relationship to the magnitude of the burst 70 in which they occur.

Trapezoid signal generator block 56 comprises a PNP transistor Q2 provided with a feedback capacitor C7 connecting its base and collector terminals to provide an integrator circuit, with its emitter forming amplitude terminal 90 of trapezoid signal generator block 56. The collector of transistor Q2, returned to ground through resistor R13, is further connected to the AM contact of switch 20 to supply trapezoid signal 16. Current is applied to the base of transistor Q2 and capacitor C7 by means of an NPN transistor Q3 having its emitter returned to ground through resistor R14 and its collector connected to the base of transistor Q2, the collector of transistor Q3 being coupled to amplitude terminal 90 by way of a resistor R15. Pulse timing signal 52 is received via resistor R16 at the base of a PNP transistor Q4, the emitter of which is coupled to +4 volts through a resistor R17 as well as to amplitude terminal 90 via resistor R18. The collector of transistor Q4 is returned to ground by way of potentiometer 64 having its movable contact connected to the base of transistor Q3 to provide a variable voltage thereat. Potentiometer 64 controls the rise rate of trapezoid signal 16 since the voltage at the base of transistor Q3 determines the charging rate of the capacitor C7.

When pulse timing signal 52 is high, transistor Q4 is off which maintains transistors Q3 and Q2 in the off condition. When a falling edge in pulse timing signal 52 is presented to block 56, transistor Q4 conducts current and causes an increase in voltage, variable by operation of the potentiometer 64, at the base of transistor Q3. As transistor Q3 begins to supply current to capacitor C7, capacitor C7 charges and transistor Q2 conducts such that trapezoid signal 16 begins a linear ramp, i.e. as illustrated for region 78 in FIG. 3. Variation of the voltage presented to the base of transistor Q3 by operation of potentiometer 64 adjusts the duration of the linear ramp. Eventually, capacitor C7 charges completely and signal 16 stabilizes at a constant magnitude, as constant region 82 of FIG. 3. When pulse timing signal 52 later presents a rising edge at the base of transistor Q4, transistor Q4 shuts off and returns the voltage present at the base of transistor Q3 to near ground potential, allowing capacitor C7 to discharge into the base of transistor Q2 and causing a falling ramp in trapezoid signal 16, linearly decreasing as indicated for region 80 of FIG. 3.

Swell timing block 96 is an IC timer IC5 configured similarly to IC1 for producing a 50% duty cycle output, the THRESHOLD and NOT-TRIGGER pins of IC5 being tied together and returned to ground through an external capacitor C8, as well as being coupled to the OUT pin of IC5 via resistor R19. Appropriate selection of the component values for resistor R19 and capacitor C8 produce swell timing signal 98 at the OUT pin of IC5 with a 1 Hz frequency.

Swell signal generator 94 receives swell timing signal 98 at the base of PNP transistor Q5 through serially connected resistor R20 and diode D2. The base of transistor Q5 is also coupled to +4 volts via resistor R21, while being connected to the collector of transistor Q5 by feedback capacitor C9 to form an integrator circuit. The emitter of transistor Q5 is tied to +4 volts and the collector of transistor Q5 is returned to ground through a resistor R22 whereby swell signal 92 may be taken from the collector of transistor Q5 and connected to the aforementioned terminal 90 of trapezoid signal generator block 56. As swell timing signal 98 changes state, swell signal 92 ramps up and down in response thereto, in order to cause the previously described amplitude variations in trapezoid signal 16. The rate of charging of the integrator circuit including capacitor C7 and transistor Q2 is regulated according to swell signal 92 received at terminal 90 between resistors R18 and R15. Thus as the signal 92 decreases, the rate of rise of the trapezoid decreases and vice versa to maintain the comparative sizes of the pulses as modulated by the trapezoid.

Amplitude modulator block 24 comprises a PNP transistor Q6, the base of which is coupled to carrier terminal 26 via resistor R23, its emitter providing modulation terminal 28, and its collector providing output terminal 30. Terminal 26 is connected to the movable contact of switch 19 to selectively receive either pulse signal 14 or FM signal 18. Terminal 28 is connected to the movable contact of switch 20 for selectively receiving either a constant +4 volts or the trapezoid signal 16.

In output amplifier block 12, the emitter-collector current of transistor Q6 is returned to ground through potentiometer P4 to provide a voltage at the potentiometer's movable contact corresponding in magnitude to the emitter-collector current of transistor Q6, i.e., the output of amplitude modulation block 24. Adjustment of potentiometer P4 provides adjustment of stimulation intensity by scaling the output. The movable contact of potentiometer P4 is coupled to the base of NPN transistor Q7 through resistor R24 while the collector of transistor Q7 is connected to the base of a PNP transistor Q8 which has its emitter tied to +6 volts and its collector tied to the emitter of transistor Q7. The base of transistor Q7 is also coupled the base of transistor Q8 via a capacitor C10. The base of transistor Q8 is coupled to +6 volts through a resistor R25. The emitter of transistor Q7 and collector of transistor Q8 are returned to ground by the primary winding of a transformer T1 such that the secondary winding of transformer T1 carries an amplified version of the signal taken from the movable contact of potentiometer P4.

A light emitting diode LD1 and a zener diode D3 are connected in parallel for coupling a first end of the secondary winding of transformer T1 to the negative skin contacting electrode 22. Light emitting diode LD1 indicates proper operation of the device, i.e., a stimulating current flowing between electrodes 22, while the diode D3 provides an alternate current path in the event the diode LD1 fails. A second end of the secondary winding of transformer T1 is coupled to the positive skin contacting electrode 22 through current limiting circuitry 100 which prevents an excess or hazardous flow of current through the electrodes. Diode D4 rectifies the current from transformer T1 to provide only positive current pulses to electrodes 22.

It is desirable to provide a user of the nerve block device with a visual indication as to which signal is being applied to the electrodes 22. This can be achieved by pulsing an LED with the stimulating signal, the flashing of the LED thereby indicating the nature of the stimulating signal. While it is possible to drive an LED lamp with a signal taken from lead 102, the voltage developed across the potentiometer P4, at high frequencies is unsuitable due to the large current required to light the LED for such a brief period, the required current typically being great enough to damage the LED.

Figure 5:
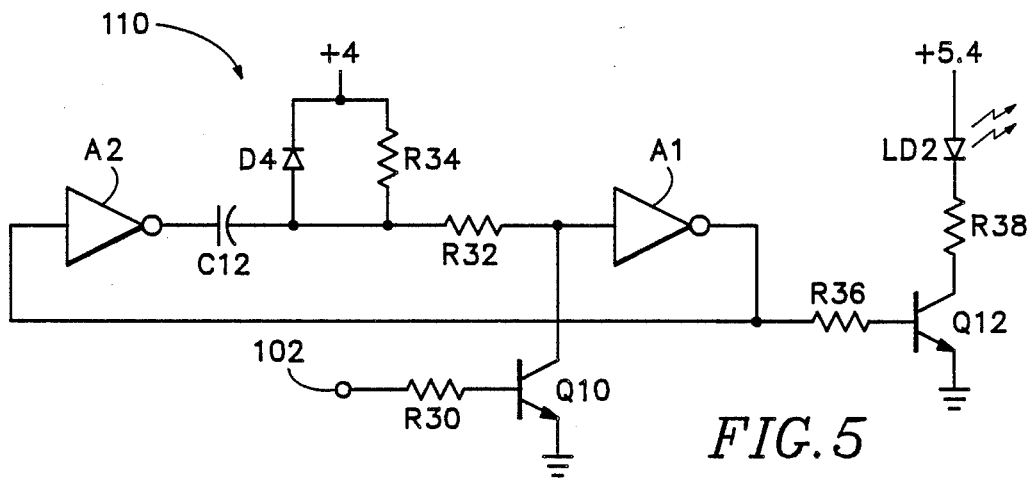
FIG. 5 illustrates a further circuit portion.

Referring now to FIG. 5, pulse stretcher circuit 110 detects high frequency voltage pulses on the lead 102 and provides a 5 mS pulse for driving LED LD2 with a non-destructive current. Pulse stretcher circuit 110 includes NPN transistor Q10 having its base connected to lead 102 via resistor R30, its emitter returned to ground, and its collector connected to the input of inverting amplifier A1. The output of inverting amplifier A1 is fed to the input of second inverting amplifier A2 while the output of inverting amplifier A2 is coupled to the input of inverting amplifier A1 through capacitor C12 in series with resistor R32. At the interconnection of capacitor C12 and resistor R32, a diode D4 and resistor R34 are connected to +4 volts in parallel. The output of inverting amplifier A1 is coupled through resistor R36 to the base of NPN transistor Q12 which has its emitter tied to ground and its collector coupled to +5.4 volts through resistor R38 and LD2 in series.

When the voltage present on lead 102 is relatively low, as between stimulating pulses, Q10 is off and the potential at the input to amplifier A1 is relatively high whereby the output of amplifier A1 is low and the output of amplifier A2 is relatively high. When the potential on lead 102 is briefly raised, transistor Q10 conducts current through resistors R34 and R32 lowering the potential at the input to amplifier A1 so that the output of amplifier A1 goes high and the output of amplifier A2 goes low, there being a difference in potential across capacitor C12. By this time the potential on lead 102 may have returned to a low level, as for high frequency stimulation signals; however, a charging current flows through resistor R34 into capacitor C12 which maintains the output of amplifier A1 high and the output of amplifier A2 low. The output of amplifier A1 remains high until capacitor C12 charges, and during this interval, approximately 5 mS, the output of amplifier A1 continues to drive transistor Q12 into conduction, lighting LD2.

The present invention generates an improved stimulation signal which allows for higher stimulation intensity, and is more difficult for the patient to adapt to, as would defeat the purpose of the stimulation. The stimulating signal provided at electrodes 22, the bursts 70 as amplified by output amplifier 12, comprises a monophasic (direct current) pulsed signal in which stimuli in bursts 70 typically have a maximum voltage of approximately 130 volts and a maximum output charge of 24 microcoulombs, e.g., 120 milliamperes for 0.2 milliseconds. Five bursts 70 are generated each second and each burst 70 includes seven stimuli or pulses, with each pulse suitably being less than 0.2 milliseconds in duration, such that the stimulating signal provided at electrodes 22 includes 35 pulses per second.

Stimuli bursts 70 offer an improved stimulation waveform in that the amplitude of the initial and final stimuli of each burst are a fixed percentage of the maximum amplitude of that burst. If pulse signal 14 and trapezoid signal 16 were not in a predetermined timed relationship, i.e., not properly timed and synchronized, the first and final stimuli of each burst could vary widely in amplitude according the instantaneous amplitude of the burst envelope in which they occur. That is, they would not be consistently equal in magnitude which may result in unpleasantness to the patient, partially defeating the effectiveness of the stimulation. In accordance with an embodiment of the present invention, each burst 70 begins with stimuli having gradually increasing amplitude and ends with stimuli having gradually decreasing amplitude, the first and last stimuli suitably having the same amplitude. It appears that a patient is able to handle a higher intensity and therefore more effective signal with such consistent waxing and waning stimuli without experiencing counter productive discomfort. The swelling of the trapezoid signal 16 further decreases the chances of the patient becoming "adapted" to the stimulating signal.

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A nerve block device comprising:
   means for producing a cyclic modulating signal of changing amplitude;
   means for producing a carrier signal in a predetermined timed relation to the modulating signal, the carrier signal having a first frequency;
   modulation means for producing a resultant signal;
   patient output electrodes;
   output means for coupling said resultant signal to said patient electrodes;
   means for producing a frequency modulated signal; and
   switch means for selectively applying one of the carrier signal and the frequency modulated signal to said modulation means and for selectively applying one of the modulating signal and a constant signal to said modulation means such that in a first state of said switch means the resultant signal corresponds in frequency to the carrier signal and in magnitude to the modulating signal amplitude while in a second state of said switch means the resultant signal corresponds in frequency to the frequency modulated signal and in amplitude to the constant signal.

2. The device according to claim 1 wherein the magnitude of the modulating signal increases linearly over a first region and decreases linearly over a second region of successive cycles thereof and wherein the first and second regions are separated by a region of constant amplitude.

3. The device according to claim 2 wherein the amplitude of the modulating signal is further amplitude modulated at a a second frequency lower than said first frequency.

4. The device according to claim 1 wherein the timed relation of the modulating signal to the carrier signal is such that a sequence of cycles of the carrier signal is initiated concurrently with production of the modulating signal.

5. The device according to claim 1 wherein the nerve block device further comprises:
   pulse stretch means responsive to the resultant signal for providing a periodic stretched pulse signal for driving a display lamp, the pulse signal having a longer time duration than the resultant signal.

6. The device according to claim 1, wherein the output means provides a monophasic pulsed direct current signal for coupling to said patient electrodes.

7. A nerve block device comprising:
   timing means for producing a periodic timing signal;
   first means receiving said timing signal for producing a periodic carrier signal wherein a sequence of carrier signal cycles is initiated in response to a given state in the timing signal;
   second means receiving the timing signal for producing a periodic modulating signal wherein each cycle of the modulating signal is initiated in response to the given state in the timing signal, said second means comprising a resistor, first current source means for providing a first current, second current source means for providing a second current, transistor means having a first terminal receiving the first current, a second terminal receiving the second current, and a third terminal coupled to a voltage source through said resistor for providing said modulating signal at the third terminal, and a capacitor coupling the second and third terminals of said transistor means for producing amplitude variations in said modulating signal;
   modulation means for producing a resultant signal corresponding in frequency to the carrier signal and corresponding in amplitude tot he modulating signal; and
   output means for amplifying the resultant signal for coupling to electrodes.

8. The device according to claim 7, wherein the output means provides a monophasic pulsed direct current signal for coupling to patient electrodes.

9. The device according to claim 7, wherein the timing signal is a square wave signal having a variable duty cycle.

10. The device according to claim 7, wherein the carrier signal is a square wave signal having a variable frequency.

11. The device according to claim 7, wherein said first means comprises:
   a carrier signal generator having a trigger input for initiating a sequence of carrier signal cycles; and synchronizing means coupled to the trigger input of said carrier signal generator and receiving the timing signal for activating the trigger input of said carrier signal generator upon detecting the given state in the timing signal.

12. The device according to claim 11, wherein said synchronizing means comprises transistor means having a first terminal coupled to the trigger input of said carrier signal generator, a second terminal coupled receive to the timing signal, and a third terminal coupled to a voltage source.

13. A device according to claim 7, wherein said first current source is variable for producing amplitude variations in said modulating signal of period longer than the period of said modulating signal.

14. The device according to claim 7, wherein said first current source comprises:
   swell means for producing a swell signal;
   a resistor;
   transistor means having a first terminal coupled to a voltage source, a second terminal coupled to a swell determining signal, and a third terminal coupled to a second voltage source through said resistor for providing the first current at the third terminal; and
   a capacitor coupling the second and third terminals of said transistor means for providing variations in the first current.

15. The device according to claim 7 wherein said second current source means is coupled to the timing signal and the magnitude of the second current varies in response to variations in the magnitude of the timing signal.

16. The device according to claim 7, wherein said modulation means comprises:
   a resistor; and
   transistor means having a first terminal coupled to the modulating signal, a second terminal coupled to the carrier signal, and a third terminal coupled to a voltage source through said resistor for providing the resultant signal.

17. The device according to claim 16, wherein said resistor is variable to provide intensity variations in the resultant signal.

18. The device according to claim 7, wherein the nerve block device further comprises:
   means for producing a frequency modulated signal; and
   switch means for selectively applying one of the carrier signal and alternatively a frequency modulated signal to said modulation means and for selectively applying one of the modulating signal and alternatively a constant signal to said modulation means such that in a first state of said switch means the resultant signal corresponds in frequency to the carrier signal and in magnitude to the modulating signal amplitude while in a second state of said switch means the resultant signal corresponds in frequency to the frequency modulated signal and in amplitude to the constant signal.

19. The device according to claim 7, wherein the nerve block device further comprises:
   pulse stretch means responsive to the resultant signal for providing a stretched pulse signal for driving a display lamp.

* * * * *